(12) United States Patent
Musbach et al.

(10) Patent No.: US 6,835,189 B2
(45) Date of Patent: Dec. 28, 2004

(54) CONTROLLED DEPLOYMENT BALLOON

(75) Inventors: Frank A. Musbach, Pleasanton, CA (US); Daniel J. Horn, Shoreview, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 67 days.

(21) Appl. No.: 10/271,830

(22) Filed: Oct. 15, 2002

(65) Prior Publication Data

US 2004/0073165 A1 Apr. 15, 2004

(51) Int. Cl.$^7$ .............................................. A61M 31/00
(52) U.S. Cl. .............................. 604/103.07; 604/916
(58) Field of Search ........................ 604/96.01, 103.06, 604/103.07, 103.11–103.13, 916, 920; 606/192, 194; 623/1.1, 1.11

(56) References Cited

U.S. PATENT DOCUMENTS

| | | | |
|---|---|---|---|
| 1,598,284 A | * | 8/1926 | Kinney ..................... 604/99.02 |
| 2,849,002 A | * | 8/1958 | Oddo ......................... 606/192 |
| 4,490,421 A | | 12/1984 | Levy .......................... 428/35 |
| 4,963,313 A | | 10/1990 | Noddin et al. .............. 264/573 |
| 5,042,976 A | | 8/1991 | Ishitsu et al. ............. 604/96.01 |
| 5,087,394 A | | 2/1992 | Keith ......................... 264/470 |
| 5,316,016 A | * | 5/1994 | Adams et al. .............. 600/587 |
| 5,348,538 A | | 9/1994 | Wang et al. ................ 604/96 |
| 5,352,199 A | * | 10/1994 | Tower ................... 604/103.07 |
| 5,403,340 A | | 4/1995 | Wang et al. ................ 606/194 |
| 5,447,497 A | | 9/1995 | Sogard et al. .............. 604/101 |
| 5,470,313 A | * | 11/1995 | Crocker et al. ........ 604/103.07 |
| 5,500,181 A | | 3/1996 | Wang et al. ................ 264/532 |
| 5,522,961 A | | 6/1996 | Leonhardt ................... 156/252 |
| 5,645,560 A | | 7/1997 | Crocker et al. ............. 606/192 |
| 5,714,110 A | | 2/1998 | Wang et al. ................ 264/529 |
| 5,749,851 A | | 5/1998 | Wang ......................... 604/96 |
| 5,843,116 A | * | 12/1998 | Crocker et al. ............. 606/192 |
| 5,948,345 A | | 9/1999 | Patel et al. ................. 264/529 |
| 5,980,532 A | * | 11/1999 | Wang ......................... 623/1.11 |
| 6,027,517 A | | 2/2000 | Crocker et al. ............. 606/192 |
| 6,120,523 A | | 9/2000 | Crocker et al. ............. 606/192 |
| 6,193,738 B1 | | 2/2001 | Tomaschko et al. ........ 606/194 |
| 6,200,325 B1 | * | 3/2001 | Durcan et al. .............. 606/108 |
| 6,287,506 B1 | | 9/2001 | Hudgins et al. ............ 264/515 |
| 6,290,485 B1 | | 9/2001 | Wang ......................... 425/470 |
| 6,296,660 B1 | * | 10/2001 | Roberts et al. ............. 623/1.11 |
| 6,328,710 B1 | | 12/2001 | Wang et al. .............. 604/96.01 |
| 6,352,551 B1 | | 3/2002 | Wang ......................... 623/1.11 |
| 6,402,778 B2 | | 6/2002 | Wang ......................... 623/1.11 |
| 6,409,741 B1 | | 6/2002 | Crocker et al. ............. 606/192 |
| 6,416,494 B1 | | 7/2002 | Wilkins .................... 604/96.01 |
| 6,458,313 B2 | | 10/2002 | Hudgins et al. ............ 264/515 |
| 6,485,666 B1 | | 11/2002 | Rowley ....................... 264/506 |
| 2002/0010441 A1 | * | 1/2002 | Horkel ........................ 604/279 |
| 2002/0077690 A1 | | 6/2002 | Wang | |
| 2002/0120320 A1 | | 8/2002 | Chen | |

FOREIGN PATENT DOCUMENTS

| | | |
|---|---|---|
| WO | 98/03218 | 1/1998 |
| WO | 02/051490 | 7/2002 |

* cited by examiner

Primary Examiner—LoAn H. Thanh
(74) Attorney, Agent, or Firm—Vidas, Arrett & Steinkrau

(57) ABSTRACT

A dilatation balloon configured and formed to have a first inflation profile at a first pressure and a second inflation profile at a second higher pressure and methods of making and using the same.

5 Claims, 2 Drawing Sheets

CONTROLLED DEPLOYMENT BALLOON

FIELD OF THE INVENTION

The present invention relates to novel balloon catheters for use in the treatment of vascular diseases and to methods of making and using the same.

BACKGROUND OF THE INVENTION

Balloon catheters are employed in a variety of medical procedures. One such procedure is angioplasty which is a well known medical practice used in the treatment of diseased arteries in the vasculature of a patient. Using angioplasty procedures, alone, however, involves a risk of re-restenosis of the artery, which may necessitate another angioplasty procedure, a surgical bypass procedure, or some method of repairing or strengthening the area. Therefore, it has become more common practice to use a catheter-delivered stent to prevent restenosis and to reinforce and strengthen weakened vessel walls. Using this procedure, a physician can implant an intravascular device, i.e. a stent, to maintain vascular patency at the site of a lesion.

A stent is typically a generally cylindrical, radially expandable device which is introduced into the vasculature of a patient using a catheter delivery assembly which typically includes an elongate shaft with a dilatation balloon mounted on its distal portion. The stent is then mounted over the dilatation balloon. The stent is maneuvered through the vasculature of the patient in a generally reduced diameter configuration, i.e. crimped. Once it has been delivered to the site of the lesion, the stent is then expanded from its reduced diameter configuration to support and reinforce the vessel walls while maintaining the vessel in an open, unobstructed condition.

Stents are well-known and widely available in both self-expanding and inflation expandable varieties. Self-expanding stents are typically maintained under positive external pressure in order to maintain their reduced diameter configuration during delivery of the stent to its deployment site. Inflation expandable stents, i.e. balloon expandable stents, are crimped to their reduced diameter about the inflation member of the stent delivery catheter and once positioned at the deployment site are expanded to a larger diameter for implantation in the vasculature by providing inflation fluid to the inflation member thus expanding the inflation member thus expanding the stent.

One problem which may arise in the case of balloon expandable stents, is commonly referred to in the industry as "watermelon seeding" in which the stent has been known to slide off the balloon during expansion. Various methods have been employed in order overcome the possibility of stent slippage during expansion.

SUMMARY OF THE INVENTION

The present invention relates to novel dilatation balloons which exhibit first and second inflation profiles, and to methods of producing the novel balloons of the present invention. The balloon has a body portion, cones and waist portions. The body of the balloon further has a proximal region and a distal region which are separated by the central region of the body. The length of the body, and the taper angle of the cone portions change from one inflation profile to the next as the pressure is increased.

The balloon has a first inflation profile achieved by inflating the balloon to a first inflation pressure and a second inflation profile which is achieved by increasing the inflation pressure to a second, higher pressure.

In one embodiment, in the first inflation profile of the balloon, the central region is inflatable to a diameter $D_1$ and at least one of the proximal and distal regions of the body portion of the balloon are inflatable to a second diameter which is less than $D_1$, $D_1'$. The diameter $D_1'$ may be taken at any of an infinitesimal number of locations between the central region of the balloon body and the cone portions. As the point at which $D_1'$ is taken approaches the central region of the body portion, the value of $D_1'$ will approach the value of $D_1$. In the second inflation profile, the central region is inflatable to a diameter $D_1''$ and the proximal and/or distal ends of the body portion of the balloon are inflatable to a diameter $D_1''$ which is substantially equal to $D_1$. It is important to note that $D_1$ may increase some nominal amount from the first inflation profile to the second inflation profile.

Thus, in the second inflation profile, the proximal region, the distal region or both, and the central region of the body portion have inflation diameters which are substantially constant along the length of the balloon body. In the first inflation profile, the proximal and/or distal ends of the body region taper into the cone regions.

The inflation of the balloon to its first inflation profile is achieved by inflation to a first pressure, and inflation to the second inflation profile is achieved by inflation to a second pressure higher than the first pressure The present invention further relates to a method of making the same, the method including a first molding step wherein the second inflation profile or configuration is formed and a second molding step wherein the first inflation profile or configuration is formed.

In a first molding step at a temperature $T_1$, the balloon is formed to have a body having a length $L_1$ and tapered cones which have an angle $Ø_1$ relative to the longitudinal axis of the balloon and in a second molding step at a temperature $T_2$ which is less than $T_1$ but higher than the $T_g$ of the material from which the balloon is being formed, the balloon is remolded to have a body with a length $L_2$ which is less than $L_1$ and tapered cones which have an angle $Ø_2$ relative to the longitudinal axis of the balloon which is less than $Ø_1$. During inflation, the balloon exhibits the configuration formed during the second molding step at a first pressure, and exhibits the configuration formed during the first molding step at a second higher pressure. The balloon is thus said to have two inflation profiles, the first inflation profile being the second remolded configuration and the second inflation profile being the first molded configuration.

During inflation, as the pressure is increased to relatively low to medium pressure during expansion, the first inflation profile or configuration is exhibited. At higher pressures, the balloon reaches its fully expanded configuration and exhibits its second inflation profile or configuration.

The dilation balloons of the present invention may be used in various medical procedures and thus come in a large range of sizes and may therefore be suitably dimensioned for their intended purpose.

The balloon catheters of the present invention are particularly useful for the delivery and implantation of stents for use in the treatment of stenotic vascular disease. Furthermore, the present invention is particularly suitable for use with inflation expandable stents wherein enhanced stent securement and safer stent loading are of concern.

Using a catheter delivery assembly, the dilatation balloon of the present invention, in combination with the stent, is positioned adjacent a treatment site in a body vessel where it is first inflated to its first inflation profile at a first pressure wherein the central region is inflated to a diameter $D_1$ and at least one of the proximal and distal ends of the body of the balloon is inflated to a diameter $D_1'$ which is less than $D_1$. The diameter $D_1'$ may be taken at any infinitesimal number of points between the central region of the body and the cone portions. The balloon is then inflated to its second inflation profile at a second higher pressure wherein the central region of the body is inflated to $D_1$, and the proximal and distal regions of the body are inflated to a diameter $D_1''$ which is substantially equal to $D_1$. However, as noted above, $D_1$, in the second inflation profile, may be nominally larger than in the first inflation profile.

The balloon of the present invention may be employed in combination with various devices including catheter delivery devices and stents, for example, and may be employed in the treatment of various diseases.

Further features and advantages of the present invention will become apparent to one of skill in the art in view of the Detailed Description of the Preferred Embodiments which follows, when considered together with the attached drawings and claims.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

Figure 1:
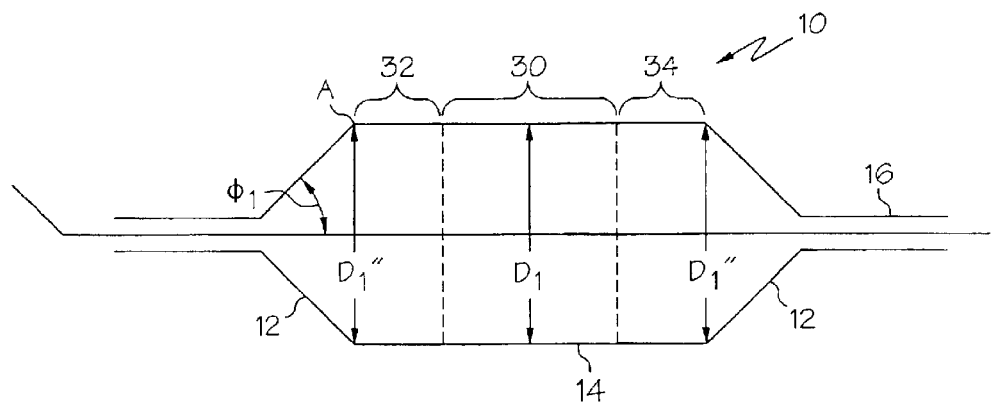
FIG. 1 shows a balloon with its second inflation profile in an expanded high pressure configuration.

FIG. 1 shows generally at 10, a dilatation balloon of the present invention in its second inflation profile. As can be seen from FIG. 1, the balloon has a uniform cylindrical body portion 14 having a central region 30, a proximal end 32, and a distal end 34, and short cones 12. This second inflation profile of the balloon is formed as a result of a first balloon formation or first molding step as employed in the method of the present invention. The balloon is in a fully expanded, high pressure profile and has a central region 30 with a diameter $D_1$ and the proximal end 32 and distal end 34 of the body each have a diameter $D_1''$ which is substantially equal to $D_1$. The diameter $D_1$ may exhibit a nominal increase from the first lower pressure configuration to the second higher pressure configuration.

The balloon formation may be carried out in any conventional manner with conventional extrusion and blowing techniques. The formation method can include the steps of extruding a tubular preform, blow molding the balloon and annealing the balloon. Each of these major process steps may in turn include a number of sub-steps. Depending on the balloon material employed, the preform may be axially stretched before it is blown. Techniques for balloon formation are discussed in U.S. Pat. No. 4,490,421 to Levy and in U.S. Pat. No. 5,348,538 issued Sep. 20, 1994 to Wang et al.

Typical molding temperatures for this first molding step are typically about 90° C. to about 100° C., and more typically about 95° C. However, this may vary depending on the type of material employed.

After the initial molding step, the balloon is typically shrunk at a temperature that is less than the temperature of the first molding step. One method of doing this is to place the balloon in a hot water bath after the initial molding step and shrink at a temperature less than that of the first molding step. The temperature of the water bath may be varied depending on how much shrinkage is desired. The higher the temperature, the more shrinkage that the balloon will exhibit. However, it is desirable that the temperature of the hot water bath be somewhat less than that of the initial molding temperature. No pressure is typically applied during the shrinking step.

Typically, the greater the shrinkage of the balloon, the later during the inflation pressure cycle that the balloon may distend.

Other techniques may be optionally employed to achieve the same results and are known to those of skill in the art.

The balloon is then placed in a second mold and reblown into a second inflation profile or configuration. Typical temperatures for this secondary process may be between about 80° C. and 85° C., more typically about 80° C. and 82° C. It is desirable that the remolding temperature is at least above the $T_g$ of the polymer, but less than the molding temperature employed in the first molding step. The pressure employed during this step is conventional in the art.

Figure 2:
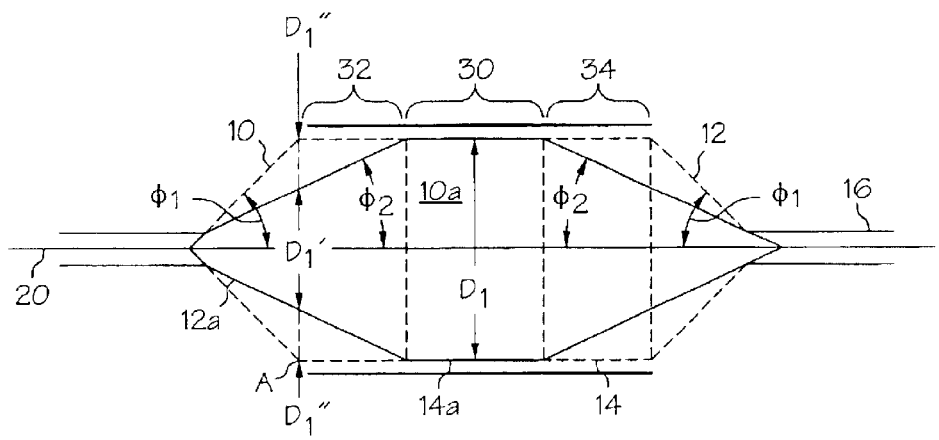
FIG. 2 shows a balloon with its first inflation profile (dashed line) in an expanded low to medium pressure configuration and its second inflation profile (solid line) in an expanded higher pressure configuration.

One embodiment of a first inflation profile 10a of the balloon of the present invention resulting from the second molding process is represented in FIG. 2 by the solid lines and may be compared to the second inflation profile 10 (also shown in FIG. 1, resulting from the first molding process, which is represented by the dotted lines in FIG. 2. The same first inflation profile is shown generally at 14a in FIG. 3. In the second molding step, the proximal and distal ends 32, 34 of the body portion taper into the cones portions 12a.

Figure 3:
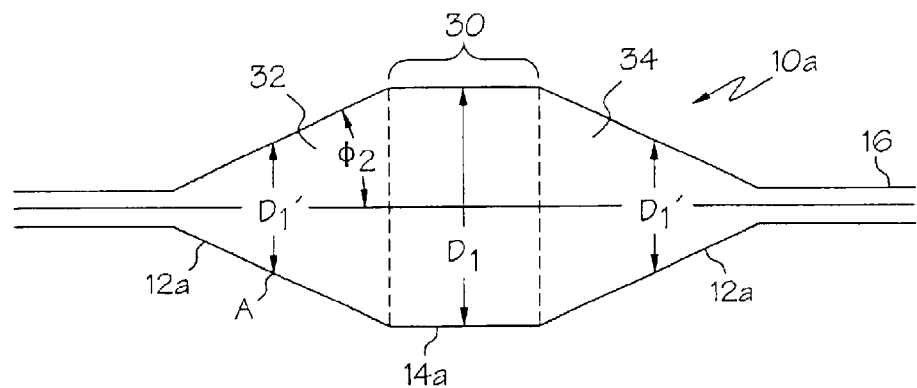
FIG. 3 shows a balloon with its first inflation profile in an expanded low medium pressure configuration.

During the first molding step, the second inflation profile of the balloon is formed with a body which has a central region 30 having a diameter $D_1$, a proximal end 32, and a distal end 34 which have a diameter $D_1'$ which is substantially equal to $D_1$, and tapered cones 12. During the second molding step in which the first inflation profile is formed, the diameter $D_1$ of the central region of the body 30 remains substantially unchanged while the diameter $D_1''$ of the proximal and/or distal ends 32, 34 of the body decreases to $D_1'$. For illustrative purposes only, as shown in FIG. 3, for example, $D_1'$ has been taken at a point A which is somewhat central between the central region of the body 30 and the cone portions 12a. However, $D_1'$ may be taken at any of an infinitesimal number of points between the cone portions 12 and the central region 30 of the body portion and will be less than $D_1$. However, the closer that the point at which $D_1'$ is taken gets to the central region 30 of the body portion, the closer the value of $D_1'$ will become to $D_1$.

In the second inflation profile, the distal and/or proximal regions can actually taper into the cone portions of the balloon.

During inflation, the balloon will exhibit the first inflation profile in its first lower pressure configuration and will exhibit the second inflation profile in its second higher pressure configuration. Thus, in the first inflation profile, the balloon will have a body having a central region with a diameter $D_1$ and at least one of the proximal and distal-ends exhibit a diameter $D_1"$ which is less than $D_1$. In the second higher pressure inflation profile, the central region 30 of balloon body has a diameter $D_1$ and at least one of the proximal and distal ends has a diameter $D_1"$ which is substantially equal to, but which may be slightly larger than $D_1$.

The first inflation profile, i.e. the configuration formed during the second molding step, opens at first use when subjected to a first pressure. With increasing pressure, the remolded body section which may be said to now become part of the tapered cones, 10*a* rapidly expands returning the balloon to first molded balloon configuration or the second inflation profile at a second higher pressure shown generally at 10 in FIG. 1. During this state, the central region and the proximal and distal ends have a substantially constant diameter along the length of the body. As the second inflation profile is formed during the first molding step, the balloon may be said to retain memory of the second molded configuration and therefore returns to this shape upon full expansion at higher pressures.

A typical pressure at which the first inflation profile is exhibited may be about 2–4 atmospheres while typical pressures at which the second inflation profile is exhibited may be about 5–12 atmospheres with 6 being typical. These ranges are for illustrative purposes only, and depending on the characteristics of the material from which the balloon is formed, the pressure of the first and second inflation profile could be higher.

During the secondary molding process, the length of the taper of the cone portion of the balloon is increased, and the angle of the taper of the cone section relative to the longitudinal axis of the ballon is changed accordingly. Taper angles for a ballon of a typical 20 mm length, $L_1$, is in the range of about 10° to about 45°, suitably about 15° to about 45°, although these angles may reach a perpendicular 90°. After the remolding in which the body portion is decreased to about a third of its original length, $L_2$, the taper angle may drop to between about 2° to about 14°, and more typically in the range of about 8° to ab t 10°. The taper angle of the cone section of the balloon relative to the longitudinal axis 20 is represented by $Ø_1$ in FIG. 2 while the taper angle of the cone section relative to the longitudinal axis after the second molding process is represented by $Ø_2$ in FIG. 2. The balloon will exhibit the taper angle, $Ø_2$, during its first inflation profile and the balloon will exhibit the taper angle $Ø_1$ during its second inflation profile. The taper angles represented in FIG. 2 are intended to be for illustrative purposes only, and are not intended to be actual angles which may be exhibited by catheter dilatation balloons.

$L_1$ may vary between about 10 mm and about 30 mm, while $L_2$ may vary between about 3 mm and 10 mm.

The above ranges are intended for illustrative purposes only, and are not intended as a limitation on the present invention.

Figure 4:
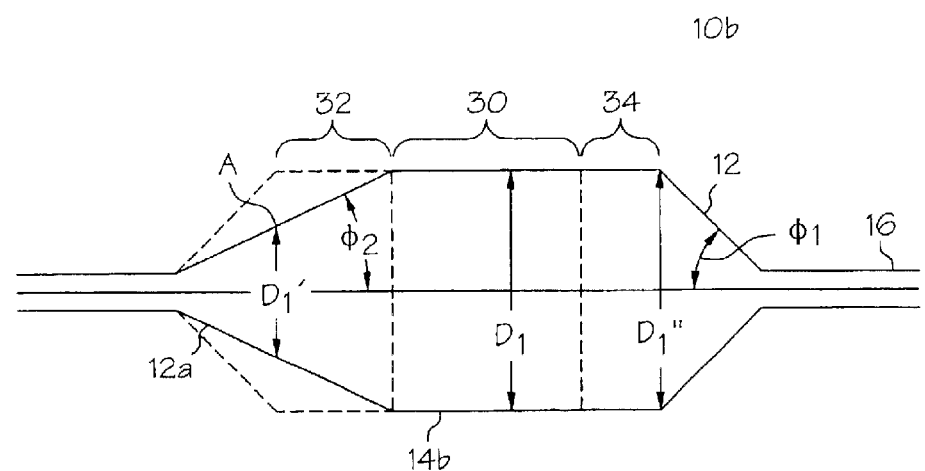
FIG. 4 shows a balloon of the present invention having an alternative first inflation profile.

FIG. 4 shows generally at 10*b*, a balloon of the present invention having an alternative inflation profile. In this inflation profile, the proximal end 32 of the balloon only and not the distal end 34 has the remolded configuration. However, it is important to note that it could be the proximal end 32, the distal end 34, or both. The second inflation profile is shown in FIG. 1. The balloon is similar in other respects to the embodiments described above.

The properties of distention, burst pressure and burst mode are not negatively impacted by the secondary molding process.

The balloons of the present invention may be formed using any materials known to those of skill in the art. Some examples of balloon materials which find utility herein include, but are not limited to, polyolefins, polyesters, polyethers, polyimides, polyamides, ionomeric polymers, polyurethanes, polycarbonates, polyvinyl chlorides, polyphenylene sulfides, block copolymer elastomers, and so forth.

More specific examples of useful polyolefins include, but are not limited to, polyethylenes and polypropylenes and any copolymers thereof.

Other specific examples of materials useful in making the balloons of the present invention include, but are not limited to, polyethylene terephthalate, acrylonitrile-butadiene-styrene copolymers, polyether-polyester copolymers, polyether polyamide copolymers, polyether block amides, and so on and so forth.

Balloon catheters embodying additional features known in the vascular dilatation art, including, but not limited to, implantable stents which are employed in various vessels in the body, drug delivery, perfusion and dilatation features, or any combination of such features may be used in combination with the dilatation balloon of the present invention.

The balloons of the present invention find particular utility for the deployment of balloon expandable stents which have what is referred to in the art as an "open cell" design. However, the use of the dilatation balloon with any stent design is contemplated herein.

In general, balloons in accordance with the present invention may be used in any and all vascular systems or cavities in the body. They may be employed in the implantation of stents in blood vessels which have collapsed, are partially occluded, blocked, weakened, or dilated for maintaining them in an open unobstructed state as well as for implanting stents in the urinary tract, bile ducts, alimentary tract, tracheobronchial tree, cerebral aqueducts, genitourinary system, prostatic urethra, fallopian tubes, as well as other regions of the body. Of course, the size of the stent as well as the balloon will depend on the application to which they are being put.

The following non-limiting examples further illustrate the present invention.

EXAMPLES

Example 1

In one example the balloon is formed of a PEBAX® 7033 polyether-block-amide. The balloon is initially molded at a temperature of about 95° C. and has a body length $L_1$ of about 20 mm and the tapered portion of the cone section has an angle $Ø_1$ of about 15° relative to the longitudinal axis of the balloon. The balloon is then placed in a hot water bath at a temperature between about 80° C. and about 82° C., and remolded at the same temperature. The balloon now has a body length $L_2$ of about 6.5 mm and the tapered portion of the cone section has an angle $Ø_2$ of about 9°.

The balloon is then inflated using increasing pressure. At 2–3 atmospheres, the balloon exhibits an inflation profile wherein the body has a length $L_2$ of about 6.5 mm and the tapered portion of the cone section has an angle $Ø_2$ of about 9°.

The pressure is then increased. At about 6 atmospheres, the balloon exhibits a second inflation profile wherein the body has a length $L_1$ of about 20 mm and the tapered portion of the cone section has an angle $Ø_1$ of about 15° relative to the longitudinal axis of the balloon.

Example 2

A balloon was formed using TRAYTUF® 7357 polyethyleneterephthalate (PET). The balloon was initially molded at a temperature of about 95° C. and had a body length, $L_1$, of about 20 mm and the tapered portion of the cone section had an angle $\emptyset_1$ of about 15° relative to the longitudinal axis. The balloon was then placed in a water bath at a temperature of 80° C. for about 10 seconds and then remolded at a pressure of 125 psi for about 45 seconds to a shape where $L_2$ is about 6.5 mm and the tapered portion of the cone section had an angle of about 9° relative to the longitudinal axis. The balloon was then inflated at 37° C. by increasing the pressure. At a pressure of between about 8 atm and 10 atm, the balloon exhibited its second inflation profile wherein the body had a length, $L_1$, of about 20 mm and the tapered portion of the cone section had an angle $\emptyset_1$ of about 15° relative to the longitudinal axis.

The above disclosure is intended for illustrative purposes only and is not exhaustive. The embodiments described therein will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A dilatation balloon having a body portion, cone portions and waist portions, said body portion further having a distal end, a proximal end, and a central region separating said distal end and said proximal end of said body portion of said ballon, said balloon configured and formed such that upon inflation to a first pressure said balloon exhibits a first inflation profile and upon inflation to a second pressure in excess of the first pressure said balloon exhibits a second inflation profile, said central region of said body portion of said balloon in said first inflation profile having a diameter $D_1$ and a substantially cylindrical geometry and at least one of said proximal and distal ends of said body portion taken at a point between said central region and said cone portions exhibiting a diameter $D_1''$ less than $D_1$;

and said central region of said body portion of said balloon having a diameter $D_1''$ which is substantially equal to $D_1$ when the balloon is inflated to the second inflation profile, and wherein diameter $D_1$ remains substantially the same from the first inflation profile to the second inflation profile.

2. The dilatation balloon of claim 1 wherein said balloon exhibits its first inflation profile when subjected to pressures of about 2–4 atmospheres.

3. The dilatation balloon of claim 1 wherein said balloon exhibits its second inflation profile when subjected to pressures of about 5–12 atmospheres.

4. A catheter assembly comprising:
a) a catheter having a distal end;
b) an unexpanded inflatable balloon mounted on said catheter near the distal end of said catheter said inflatable balloon having a body portion with a central region, a distal end and a proximal end, and cone portions and waist portions and said balloon configured and formed to have a first inflation profile at a first pressure and upon inflation to a second pressure in excess of the first pressure said balloon exhibits a second inflation profile, said central region of said body portion of said balloon in the first inflation profile having a diameter $D_1$ and a substantially cylindrical geometry and at least one of said proximal and distal ends of said body portion exhibiting a diameter $D_1'$ which is less than $D_1$ wherein $D_1'$ is taken at a point A between said central region of said body portion and said cone portions, $D_1'$ approaching $D_1$ as point A approaches said central region;

and said central region of said body portion of said balloon having a diameter $D_1$, and at least one of said proximal end and said distal end having a diameter $D1''$ which is substantially equal to $D_1$ when the balloon is inflated to the second inflation profile and wherein diameter $D_1$ remains substantially the same from the first inflation profile to the second inflation profile;

c) a stent mounted on said catheter over said balloon unexpanded balloon.

5. A method of implanting a tubular stent within a body lumen using a controlled deployment balloon the balloon having a body having a proximal end, distal end, and a central region separating said proximal end and said distal end of said body, and cone portions and waist portions, the method comprising the steps of:

providing an elongate tubular catheter assembly having an inflatable balloon mounted thereon, said balloon having a first inflation profile at a first inflation pressure and a second inflation profile at a second higher inflation pressure;

positioning an expandable tubular stent on the balloon;

positioning the balloon within a body lumen adjacent a treatment site;

inflating the balloon to the first inflation profile characterized in that the central region of said body portion has a diameter $D_1$ and a substantially cylindrical geometry, and at least one of said proximal and said distal end have a diameter $D_1'$ taken at a point A between said central region of said body and said cone portions which is less than $D_1$, $D_1'$ approaching $D_1$ as point A approaches said central region of said body portion;

increasing the inflation pressure to a second higher inflation pressure to further expand the stent such that said balloon inflates to the second inflation profile characterized in that the central portion of said body has a diameter $D_1$ and at least one of said proximal end and said distal end have a $D_1''$ taken at point A which is substantially equal to $D_1$ and wherein diameter $D_1$ remains substantially the same upon inflation from the first inflation profile to the second inflation profile.

* * * * *

UNITED STATES PATENT AND TRADEMARK OFFICE
CERTIFICATE OF CORRECTION

| | |
|---|---|
| PATENT NO. | : 6,835,189 B2 |
| APPLICATION NO. | : 10/271830 |
| DATED | : December 28, 2004 |
| INVENTOR(S) | : Horn Musbach |

It is certified that error appears in the above-identified patent and that said Letters Patent is hereby corrected as shown below:

Column 7, Line 33, delete "ballon" and insert -- balloon --;

Column 7, Line 43, delete "$D_1$"" and insert -- $D_1$' --

Column 7, Line 44, delete "said central region" and insert -- at least one of said proximal end and said distal end --;

Signed and Sealed this

Seventeenth Day of October, 2006

JON W. DUDAS
*Director of the United States Patent and Trademark Office*